United States Patent [19]

Nudelman et al.

[11] 3,932,398
[45] Jan. 13, 1976

[54] 3-HALO-CEPHAM DERIVATIVES

[75] Inventors: Abraham Nudelman, Bala Cynwyd; Ronald J. McCaully, Malvern, both of Pa.

[73] Assignee: American Home Products Corporation, New York, N.Y.

[22] Filed: Apr. 19, 1973

[21] Appl. No.: 352,850

[52] U.S. Cl.......... 260/243 C; 424/246; 260/239.1; 424/271
[51] Int. Cl.².............. C07D 501/18; C07D 501/10
[58] Field of Search ............................. 260/243 C

[56] References Cited
UNITED STATES PATENTS

| | | | |
|---|---|---|---|
| 3,275,626 | 9/1966 | Morin et al. | 260/243 C |
| 3,668,201 | 6/1972 | Gutowski | 260/243 C |
| 3,725,397 | 4/1973 | Graham et al. | 260/243 C |
| 3,725,399 | 4/1973 | Ellerton et al. | 260/243 C |

Primary Examiner—Nicholas S. Rizzo
Attorney, Agent, or Firm—Richard K. Jackson

[57] ABSTRACT

Penicillin sulfoxides are converted to 3-halo-3-methyl-cepham-4-carboxylic acid esters and amides or the corresponding cephem derivatives by heating the penicillin sulfoxide precursor in a polyhaloalkane solvent to a temperature between 50° to about 150°C. in the presence of an equimolar amount of a neutral or basic catalyst, respectively. The catalysts employed are bases such as pyridine, picoline, lutidine, quinoline, isoquinoline, dimethylaniline or a quaternary ammonium salt. The 3-halo-cepham intermediates produced with a quaternary ammonium catalyst are dehydrohalogenated to afford known cephem derivatives or converted to the free 4-carboxylic acid and the alkali metal, alkaline earth metal or ammonium salts thereof to afford novel antibacterial agents.

2 Claims, No Drawings

3-HALO-CEPHAM DERIVATIVES

BACKGROUND OF THE INVENTION

The conversion of penicillin sulfoxides to desacetoxy cephalosporins has been accomplished in poor yield in refluxing toluene or xylene in the presence of an acid such as p-toluene sulfonic acid or acetic anhydride. Morin et.al., U.S. Pat. No. 3,275,626. Analogous processes are disclosed in U.S. Pat. Nos. 3,647,787; 3,668,202; and Belgium Pat. Nos. 747,119, 747,120 and 763,104. The reaction has been considered to proceed through cleavage of the sulfurcarbon bond of the thiazolidine ring of penicillin to afford an unsaturated sulfenic acid, and possibly an intermediate anhydride or protonated sulfenic acid, which ring closes with the olefinic unsaturation to form a sulfonium ion, the latter being subject to attack by an anion to open the sulfonium ring in the production of a cephalosporin derivative or a substituted penam system. Barton et.al., J. Chem. Soc. (London) (C), pp. 3540–3550 (1971). It is known that isothiazoles result from treatment of a penicillin sulfoxide ester with triethylamine or pyridine Morin et.al. J.A.C.S. 91, 1401 (1969); Barton et.al., supra at page 3542.

DESCRIPTION OF THE INVENTION

In accordance with this invention, there is provided a process for converting penicillin sulfoxides to cephalosporin derivatives which comprises heating the penicillin sulfoxide precursor in an inert polyhaloalkane solvent to a temperature between 50° to about 150°C. for a period of from 10 to 50 hours in the presence of at least an equimolar amount of a neutral or basic catalyst.

A second process aspect of this invention provides a process for dehydrohalogenating the 3-halo-3-methyl-cepham derivatives to obtain the corresponding known cephem derivatives which comprises heating the 3-halo cepham in the presence of a base selected from the group consisting of pyridine, 1,5-diazabicyclo[4.3.0]-non-5-ene, 1,8-diazabicyclo[5.4.0]undec-7-ene, 1,8-bis[dimethylamino]naphthalene, 4-dimethylaminopyridine, triethylamine, an alkali metal carbonate, sodium acetate and silver acetate in an inert organic solvent at a temperature from about −20° to about 50°C. for a period up to about 24 hours. By selection of the reaction conditions and reagent, the reaction can be made to occur instantaneously upon dissolution of the 3-halo-cepham. The product cephem is recovered by removal of the salt by-product, removal of the solvent, followed by crystallization from an appropriate solvent or by chromatographing the product residue, employing known techniques. Thus, the 3-halo-3-methyl-cepham-4-carboxylic acid esters and amides of this invention are intermediates readily convertible to cephalosporin derivatives of known antibacterial activity.

A third process aspect of this invention provides a process for selectively deacylating the 7-amido group of a 3-halo-3-methyl-cepham-4-carboxylic acid ester or amide which comprises introducing a stoichiometric excess of $PCl_5$ to a solution of the 3-halo-cepham followed by the introduction of a tertiary amine base selected from the group consisting of pyridine, picoline, quinoline, isoquinoline, lutidine, and an N,N-di(-lower)alkylaniline, preferably dimethylaniline, at a temperature between about −35°C. and ambient temperature. The iminochloride product is solvolyzed and precipitated by sequential treatment with a lower alkanol, such as methanol, and water to afford the hydrochloride of the 7-amino-3-halo-cepham derivative. The 7-amino group may be then readily acylated by known means with known acyl groups to tailor the compound as desired.

The 4-carboxylic acid ester or amide group employed to protect the carboxylic acid during the processes described, may be any protective group known to the art. After rearrangement of the penicillin sulfoxide to either the 3-halo-cepham or the cephem derivative, the ester or amide function is readily removed, if desired, by conventional techniques such as hydrogenolysis to afford the free carboxylic acid which may then be tailored to yield a more desirable carboxylic acid salt, ester or amide for further processing or for a specific pharmaceutical application. Likewise, acid addition salts of the cephalosporin derivatives, where applicable and desired are produced by known techniques employing such pharmaceutically acceptable organic and inorganic acids as hydrochloric, hydrobromic, sulfuric, nitric, phosphoric, acetic, benzenesulfonic, toluene sulfonic, methanesulfonic, ethanesulfonic acids, and the like.

The compound aspect of this invention involves the intermediate 3-halo-3-methyl-cepham derivatives of the formula:

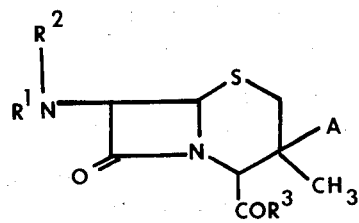

in which $R^1$ represents hydrogen or an organic acyl radical found in penicillin and cephalosporin derivatives including the aliphatic, cycloaliphatic, aromatic and heterocyclic acyl radicals of known penicillins. Specific examples of $R^1$ are —H, acetyl, phenylacetyl, α-aminophenyl acetyl, phenoxyacetyl, thiophenoxyacetyl, 2-thienylacetyl, tetrazolylacetyl, cyanoacetyl, sydnone-3-acetyl, pyridylthioacetyl, alpha-hydroxyphenylacetyl, and alpha-hydroxy-2-thienylacetyl, $R^2$ represents hydrogen or a radical that in conjunction with $R^1$ N may form a phthalimido radical, or

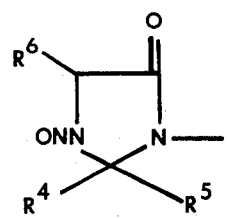

in which $R^4$ and $R^5$ are hydrogen or a lower alkyl group and $R^6$ is phenyl or 1,4-cyclohexadienyl;

R³ is a member selected from the group consisting of hydroxy, lower alkoxy, 2,2,2-trichloroethoxy, aryloxy of 6 to 10 carbon atoms, aralkoxy of 7 to 12 carbon atoms, alkoxyaralkoxy of 9 to 14 carbon atoms, mono- or di-lower alkylamino, arylamino of 6 to 10 carbon atoms, saccarimido, and phthalimido, and OM where M is an alkali metal cation, an alkaline earth metal cation or the ammonium cation;

A is a member selected from the group consisting of —Cl, —Br and —I; and the pharmaceutically acceptable acid addition salts thereof.

Within the compound aspect of this invention is the preferred group of 3-halocepham derivatives of the formula

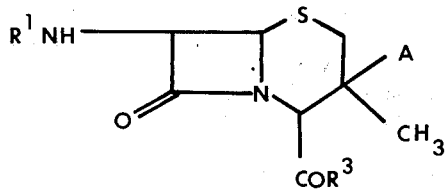

in which
R¹ is a member selected from the group consisting of —H, phenylacetyl and 2-thienylacetyl;

R³ is a member selected from the group consisting of —OH and p-nitrobenzyloxy and A is a member selected from the group consisting of —Cl and —Br.

The 3-halocepham derivatives exhibit antibacterial activity when either in the form of the free 4-carboxylic acid or its alkali metal, alkaline earth metal or ammonium salt, against gram-positive and gram-negative test organisms as well as penicillin resistant staphlococcus at an inhibitory concentration at or below 250 micrograms per milliliter using the well known and scientifically accepted agar serial dilution testing technique. Thus, the compounds of this invention are useful in the fields of comparative pharmacology and in microbiology and may be used as growth promotors in animals and for the treatment of infections amenable to treatment with penicillins and cephalosporins.

The catalyst employed in the first process aspect of this invention is a tertiary amine base selected from the group consisting of pyridine, picoline, quinoline, isoquinoline, lutidine, and N,N-di(lower)alkylaniline or a quaternary ammonium salt catalyst which presents the structural formula

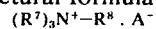

in which the groups
R⁷ and the nitrogen atom to which they are attached represent a tertiary amine, the R⁷ substituents being indepently selected from the group consisting of lower alkyl, aryl of 6 to 10 carbon atoms, aralkyl of 7 to 12 carbon atoms or the three R⁷ groups taken with the nitrogen atom to which they are attached represent an aromatic or cycloaliphatic ring structure selected from the group consisting of pyridine, 2-, 3-, or 4-picoline, quinoline, isoquinoline, lutidine, and an N,N-di(lower)alkylaniline;

R⁸ represents a quaternizing substituent selected from the group consisting of
—CH₂CH₂Y in which
Y is a group displaceable as an anion or a free base. Thus Y may be a halogen, an acyloxy group, an azide, or a quaternary ammonium group. Hence, Y may be chloro, bromo, iodo, p-toluenesulfonyl, lower alkanoyloxy, azido, thioacetoxy, pyridinium, and the like;

2,4-dinitrophenyl, 2,6-pyrimidinyl, and cyanuryl radicals; and

A represents a halo anion, and when Y represents a quaternary ammonium group there is of necessity an additional halo anion associated with the diquaternary ammonium salt.

When the first process aspect of this invention is performed in the presence of the above described quaternary ammonium salts containing the group —CH₂CH₂Y, the product is a 3-halocepham, whereas performance of the process in the presence of a tertiary amine or a quaternary ammonium salt devoid of the —CH₂CH₂Y group leads directly to the corresponding dehydrohalogenated cephem.

Thus, the process of this invention provides a means for converting penicillin sulfoxides to desacetoxy cephalosporin derivatives directly or via a 3-halo-3-methyl-cepham intermediate depending upon the catalyst employed. The use of a tertiary amine base catalyst conducts the reaction directly to the cephem product while the quaternary ammonium derivative of the tertiary amine base containing the quaternizing substituent —CH₂CH₂Y, affords the 3-halo-cepham product. In either event, the use of a polyhaloalkane solvent serves to assist in the reaction to the extent that by-product formation is either completely avoided when employing the quaternary ammonium salts or markedly reduced when a free tertiary amine base is employed as the catalyst. Hence, the critical aspects of the first process aspect of this invention resides in the catalyst and in the reaction solvent.

It is preferred to employ approximately an equimolar amount of catalyst and penicillin sulfoxide although up to a molar excess of the catalyst may be used without deleterious effect. However, a large excess of the basic catalyst is to be avoided. In those cases where the catalyst is a tertiary amine, it should be as sterically unhindered as possible. The preferred tertiary amine bases in decreasing order of preference are: pyridine, 4- and 3-picoline, quinoline, 2-picoline, lutidine, and dimethylaniline.

The intermediate penicillin sulfoxides are known compounds and are illustrated by the formula:

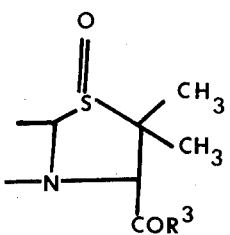

in which
R represents a member selected from the group consisting of methyl, benzyl, phenoxymethyl, thiophenoxymethyl, 2-thienylmethyl, tetrazolylmethyl, cyanomethyl, sydnone-3-methyl, pyridylthiomethyl, alpha-hydroxybenzyl and alpha-hydroxy-2-thienylacetyl; and $R^2$ and $R^3$ are described above.

Although applicants do not intend to be limited by any specific reaction theory, it is believed that the 3-halocepham intermediate is also formed when the process is performed in the presence of a tertiary amine catalyst. This conclusion is based upon the fact that the tertiary amine catalysts react with the polyhaloalkane solvents at about the same rate as is required for the overall conversion of the penicillin sulfoxide to the final cephem product, while the formation of the intermediate 3-halocepham occurs faster in the presence of a quaternary ammonium salt containing the omega-haloalkane moiety. Thus, it is hypothesized that sufficient free tertiary amine is present in the polyhaloalkane solvent at any given time during the reaction to cause dehydrohalogenation of the 3-halo cepham. Thus, from applicants observations that (1) the conversion of penicillin sulfoxides to a cephem product in the presence of a pure base procedes only with poor yield in solvents other than polyhaloalkanes, (2) the reaction in the presence of a pure base and a polyhaloalkane solvent affords the cephem in good yields, (3) the conversion of a penicillin sulfoxide to a 3-halo cepham proceeds faster in the presence of the described quaternary ammonium salts than the formation of the salts from the amine and solvents, and (4) the rate of formation of a quaternary ammonium salt in the absence of a sulfoxide is similar to the rate of formation of the cephem derivatives in the presence of a sulfoxide; it is assumed that the tertiary amine catalyst is at least partially converted to a quaternary ammonium salt by reaction with the solvent according to the equation:

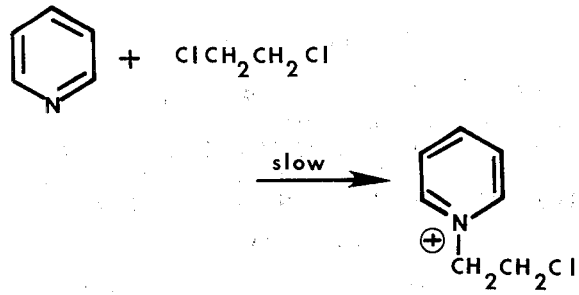

which salt directs the reaction

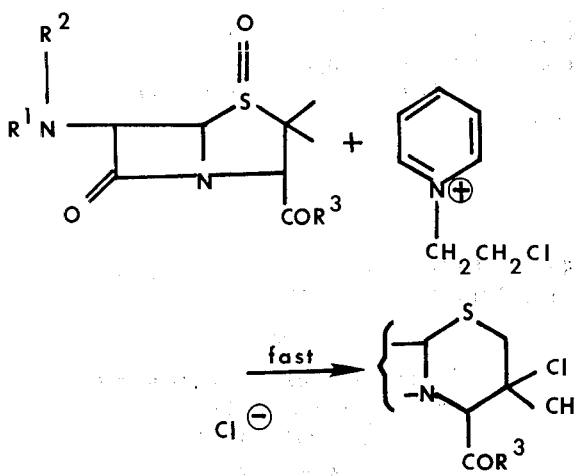

which intermediate readily dehydrohalogenates in the presence of the tertiary amine to afford the cephem product without a large formation of the isothiazole by-product observed by Morin et.al., supra.

Therefore, the solvent employed in the first process aspect of this invention is considered to be critical. The solvents are polyhaloalkanes of 1 to 4 carbon atoms in a straight chain containing two or more halo-substituents, the halo groups being chlorine, bromine or iodine. Examples of the solvents are dibromomethane, 1,2-dichloroethane, 1,2-dibromoethane, 1,2-diiodoethane, 1-bromo-2-chloroethane, 1,2-dichloropropane, 1,3-dibromopropane, 1,1,4-trichlorobutane, 1,2-dichlorobutane, 1,3-dichlorobutane, 1,1,2-trichloroethane, and the like. As indicated above, solvents other than the polyhaloalkanes may be used, such as acetonitrile, nitromethane, dioxane, dimethoxyethane, and the like, with an attending decrease in the yield of cephalosporin product.

The reaction is carried out by mixing the penicillin sulfoxide with the catalyst in such a molar ratio that there is at least one mole of catalyst per mole of sulfoxide in the solvent system, and heating the reaction mixture for from 10 to about 50 hours at temperatures ranging between 50° and 150°C., preferably for 15 to 30 hours at 70° to 120°C.

The cephalosporin products, both the 3-halo derivative as well as the dehydrohalogenated product, may be recovered by removal from the solvent followed by chromatographic separation or crystallization from a suitable solvent system.

Throughout this specification reference to "lower" alkyl groups is intended to embrace straight and branched chain univalent aliphatic hydrocarbon radicals containing from 1 to 6 carbon atoms.

The following examples are presented by way of illustration and are not to be construed as limitations on the scope of the contribution.

EXAMPLE 1

1-(2-Chloroethyl)pyridinium Chloride.

A solution of pyridine (100 g, 1.25 mole) in 800 ml. of 1,2-dichloroethane was refluxed for 72 hours. The white crystalline material which formed was filtered, washed repeatedly with fresh 1,2-dichloroethane and dried. Collected 200 g (89 per cent yield), nmr ($D_2O$) ppm (δ), 4.3 (t, 3), 5.6 (t, 3), 8.1 – 9.3 (m, 5).

EXAMPLE 2

1-(2-Bromoethyl)quinolinium Bromide

A solution of quinoline (20 ml) in 200 ml of 1,2-dibromoethane was heated under nitrogen at 70°C. for 18 hours. The crystalline solid was filtered, washed with dichloromethane and recrystallized from methanol-ether. Collected 32 g (65 per cent yield) m.p. 205°–207°C. Nmr ($D_2O$) 4.22 (t, 2), 5.63 (t, 2), 7.8 – 8.6 (m, 5), 9.1 – 9.6 (m, 3).

EXAMPLE 3

3-Chloro-3-methyl-8-oxo-7-(2-phenylacetamido)-5-thia-1-azabicyclo[4.2.0]octane-2-carboxylic acid p-nitrobenzyl ester.

To a solution of 6-(2-phenylacetamido)penicillanic acid p-nitrobenzyl ester 1-oxide (5 g, 10.3 mmoles) in 2,400 ml. of dry 1,2-dichloroethane was added 1-(2-chloroethyl)-pyridinium chloride (3.8 g, 21.3 mmoles). The mixture was heated to reflux for 21 hours, it was then concentrated to 500 ml., washed with water, treated with charcoal, dried and flash evaporated. The residual oil was dissolved in dichloromethane and the solution obtained was added to pentane. A light yellow solid was obtained (4.36 g, 83 per cent yield), which was further recrystallized from dichloromethane-pentane, m.p. 134°–136°C., nmr (DCCl₃) ppm (δ), 1.63 (s, 3, 3-methyl), 3.12 (ABq, δ 0.925 ppm, J 15 cps, 2—CH₂),

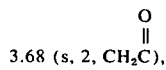
3.68 (s, 2, CH₂C), 4.80 (s, 1, 4—H), 5.16 (d, 1, 6H), 5.30 (s, 2, 0—CH₂), 5.68 (q, 1, 7H), 6.6 (d, 1, NH), 7.30 (s, 5, C₆H₅), 7.95 (ABq, δ 0.75 ppm, J 9 cps, p—NO₂—C₆H₄).

Elemental Analysis for C₂₃H₂₂ClN₄O₆S (mw 503.96); Calc'd: C, 54.81; H, 4.40; N, 8.34; Cl, 7.04; S, 6.36. Found: C, 54.42; H, 4.59; N, 7.95; Cl, 7.08; S, 6.49.

EXAMPLE 4

3-Bromo-3-methyl-8-oxo-7-(2-phenylacetamido)-5-thia-1-azabicyclo[4.2.0]octane-2-carboxylic acid p-nitrobenzyl ester.

Method I

To a solution of 6-(2-phenylacetamido)penicillanic acid p-nitrobenzyl ester 1-oxide (1 g, 2.06 mmoles) in 100 ml. of dry 1,2-dibromoethane was added 1-(2-bromoethyl)pyridinium bromide (1.13 g, 4.2 mmoles). The mixture was heated at 90°C. for 10 hours. The solvent was flash evaporated and the residue was chromatographed on 25 g. of silica gel eluted with ether. The residue obtained after evaporated of the eluent was crystallized from dichloromethane pentane to give 300 mg (26.4 per cent yield) of the title compound, m.p. 136°–137.5°C.; nmr (DMSO–D₆) ppm (δ), 1.81 (s, 3, 3—CH₃), 3.1 (ABq, δ 0.775 ppm, J 15 cps, 2-cps, 2—CH₂),

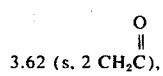
3.62 (s, 2 CH₂C), 4.86 (s, 1, 4—H), 5.23 (d, 1, 6H), 5.70 (s, 2, 0—CH₂), 5.60 (q, 1, 7H), 6.57 (d, 1, NH), 7.32 (s, 5, C₆H₅), 7.90 (ABq, δ 0.725 ppm, J 9 cps, p—NO₂—C₆H₄).

Elemental Analysis for C₂₃H₂₂BrN₃O₆S (mw 548.45): Calc'd: C, 50.37; H, 4.04; N, 7.66; Br, 14.57. Found: C, 51.20; H, 4.15; N, 7.76; Br, 14.67.

The nmr spectrum indicated a small amount of dehydrohalogenated product, which accounts for the high C analysis.

Method II

To a solution of 6-(2-phenylacetamido)penicillanic acid p-nitrobenzyl ester 1-oxide (2.42 g, 5 mmoles) in 150 ml of 1,2-dibromethane was added 1-(2-bromoethyl)quinolinium bromide (1.6 g, 5 mmoles). The mixture was heated for 16 hours at 85°C. The solvent was washed with water, mixed with charcoal, dried over magnesium sulfate and flash evaporated to an oil which was chromatographed on 40 g. of silica gel eluted with ether. The desired product crystallized in the eluent. Collected 1.32 g. (48 per cent yield) mp. and nmr were identical to those described in Method I.
Found: C, 50.80; H, 4.02; N, 7.69.

Method III

When this reaction was carried out under the same conditions as those described in Method I but replacing the 1,2-dibromoethane solvent for dibromomethane the desired title compound was obtained in lower yield.

Method IV

The title compound was also prepared in lower yield when the reaction was carried out under the same conditions as those described in Method I but replacing the 1-(2-bromoethyl)pyridinium bromide by 1,1'-ethylene bis(pyridinium bromide).

EXAMPLE 5

3-Chloro-3-methyl-8-oxo-7-(2-phenylacetamido)-5-thia-1-azabicyclo[4.2.]octane-2-carboxylic acid.

3-Chloro-3-methyl-8-oxo-7-(2-phenylacetamido)-5-thia-1-azabicyclo[4,2,0]octane-2-carboxylic acid p-nitrobenzyl ester (1.06 g, 2.1 mmoles) was hydrogenated in 60 ml of ethyl acetate over 1 g. of 10 per cent palladium on charcoal. The catalyst was filtered and washed with ethyl acetate. The filtrate was extracted with ice cold saturated sodium bicarbonate (100 ml.). The aqueous phase was covered with fresh ethyl acetate (100 ml.) and was acidified with concentrated hydrochloric acid to pH 1.5. The organic phase was separated, dried and flash concentrated to a total of 10 ml. The obtained solution was added to pentane to give 475 mg. (61 per cent yield) of the desired acid, which did not melt but slowly decomposed above 90°C., nmr (DMSO-D₆) ppm (δ), 1.75 (s, 3, CH₃), 3.32 (ABq, δ 0.675 ppm, J 14.2 cps, 2—CH₂),

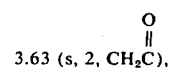
3.63 (s, 2, CH₂C), 4.55 (s, 1, 4—H), 5.22 (2, 1, 6H), 5.51 (q, 1, 7H), 7.34 (s, 5, C₆H₅), 9.1 (d, 1, NH).

Elemental Analysis for C₁₆H₁₇ClN₂O₄S (mw 368.81): Calc'd: C, 52.10; H, 4.65; N, 7.60; Cl, 9.60; S, 8.70. Found: C, 52.00; H, 4.60; N, 7.48; Cl, 9.29; S, 8.29.

EXAMPLE 6

3-Bromo-3-methyl-8-oxo-7-(2-phenylacetamido)-5-thia-1-azabicyclo[4.2.0]octane-2-carboxylic acid.

The title compound was prepared in 65 per cent yield from the p-nitrobenzyl ester by the same procedure as that described in Example 5, nmr (DCCl₃) ppm (δ), 1.83 (s, 3, CH₃), 3.18 (ABq, δ 0.875 ppm, J 10 cps, 2—CH₂),

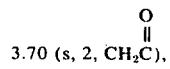
3.70 (s, 2, CH₂C), 4.81 (s, 1, 4H), 5.28 (d, 1, 6H), 5.60 (q, 1, 6H), 7.15 (d, 1, NH), 7.40 (s, 5, C₆H₅).

EXAMPLE 7

3-Methyl-8-oxo-7-(2-phenylacetamido)-5-thia-1-azabicyclo[4.2.0]oct-2-ene-2-carboxylic acid, p-nitrobenzyl ester.

Method I

To a solution of 6-(2-phenylacetamido)penicillanic acid p-nitrobenzyl ester 1-oxide (1.2 g, 2.47 mmole) in 100 ml. of 1,2-dichloroethane was added pyridine (200 mg, 2.47 mmoles). The solution was heated to reflux for 29 hours, it was then washed with dilute hydrochloric acid and water, treated with charcoal, dried and flash evaporated. The residual oil was chromatographed on 25 g. of silica gel using 2:1 diethyl ether: dichloromethane as eluents. Evaporation of the combined eluents gave 0.51 g. (45 per cent yield), of the title compound, mp and nmr identical to the literature values; and 0.26 g. (22 per cent yield) of the known isomer α-isopropylidene-3-oxo-4-(2-phenylacetamido)-4 -isothiazoline-2-acetic acid p-nitrobenzyl ester.

Method II

When this reaction was carried out under the same conditions of Method I but replacing the pyridine by other amines such as picolines, lutidine, quinoline, etc., larger amounts of the isothiazoline isomer and small amounts of the title compound were isolated.

Method III

When this reaction was carried out under the same conditions of Method I but replacing the pyridine by such salts as 1-(2,4-dinitrophenyl)pyridinium chloride, cyanuryl pyridinium chloride, 1-(6-chloropyrimidin-2-yl)pyridinium chloride, varying amounts of the title compound and the isothiazoline isomer were isolated.

Method IV

When this reaction was carried out under the same conditions of Method I but using different solvents such as dioxane, 1,2-dimethoxyethane, acetonitrile, nitromethane, trichloroethylene, lower yields of the title compounds and higher yields of the isothiazoline isomer were obtained.

EXAMPLE 8

7-Amino-3-chloro-3-methyl-8-oxo-5-thia-1-azabicyclo[4.2.0]octane-2-carboxylic acid p-nitrobenzyl ester.

To an ice cold solution of 3-chloro-3-methyl-8-oxo-7-(2-phenylacetamido)-5-thia-1-azabicyclo[4.2.0]octane-2-carboxylic acid, p-nitrobenzyl ester (5.04 g, 10 mmoles) in 100 ml of dichloromethane, are added in rapid succession phosphorus pentachloride (3.1 g, 15 mmoles) and N,N-dimethylaniline (1.8 g, 15 mmoles). The mixture is stirred at 0°C. for 15 minutes and at 25°C. for 3 hours, then 30 ml. of absolute methyl alcohol is added and the solution is further stirred for 1 hour. The solvent is flash evaporated. To the residue are added 25 ml. of ethyl acetate and 30 ml. of water and the mixture is stirred thoroughly. The crystalline solid thus obtained is filtered and air dried to give 2.75 g (65.2 per cent yield) of product, which decomposes above 160°C. NMR (DMSO-$D_6$) ppm (δ), 1.74 (s, 3,3-$CH_3$), 3.38 (ABq, δ 0.45 ppm, J 9 cps, 2—$CH_2$), 4.92 (s, 1, 4H), 5.0 (d, 1, 6H), 5.34 (d, 1, 7H), 5.51 (s, 2, $CO_2CH_2$ ), 8.05 (ABq, δ 0.525 ppm, J 5 cps, p-$NO_2$—$C_6H_4$).

Elemental Analysis for $C_{15}H_{16}N_3ClO_5S.HCl.\frac{1}{2}H_2O$: Calc'd: C, 41.77; H, 4.21; N, 9.74. Found: C, 41.54; H, 4.11; N, 9.80.

EXAMPLE 9

3-Chloro-3-methyl-8-oxo-7-[2-(2-thienyl)acetamido)]-5-thia-1-azabicyclo[4.2.0]octane-2-carboxylic acid, p-nitrobenzyl ester.

To a mixture of 7-amino-3-chloro-3-methyl-8-oxo-5-thia-1-azabicyclo[4.2.0]octane-2-carboxylic acid, p-nitrobenzyl ester, hydrochloride (1.05 g, 2.5 mmoles) and 2-thienylacetyl chloride (0.4 g, 2.5 mmoles) in 50 ml. of dichloromethane, N,N-dimethylaniline (0.61 g, 5 mmoles) is added. The mixture is stirred at 0°C. for 1 hour and is then washed with ice cold 1N hydrochloric acid, and ice cold water. The organic phase is dried, decolorized with charcoal, concentrated to 10 ml. and added to vigorously stirred pentane. The product 1.04 g (86 per cent yield) is obtained as a white powder which decomposes about 70°C. NMR (DMSO-$D_6$) ppm (δ) 1.69 (s, 3, 3—$CH_3$), 3.28 (ABq, δ, 0.575 ppm, J 11 cps, 2-$CH_2$),

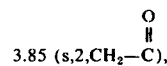
3.85 (s,2,$CH_2$—C), 4.86 (s, 1, 4-H), 5.25 (d, 1, 6H), 5.42 (s, 2, $CO_2CH_2$), 5.53 (d, 1, 7H), 7.0 (m, 2), 7.4 (m, 1) (2-thienyl), 8.04 (ABq, δ 0.575 ppm, J 5 cps, p-$NO_2$—$C_6H_4$).

Elemental Analysis for $C_{21}H_{20}N_3ClO_6S_2$: Calc'd: C, 49.46; H, 3.95; N, 8.24. Found: C, 49.43; H, 3.92; N, 8.01.

Similarly, analogous deacylated 7-amino-3-chloro-3-methyl-8-oxo-5-thia-1-azabicyclo[4.2.0]octane-2-carboxylic acid esters and amides are reacylated in 7-position by the technique illustrated in Example 9 to introduce an acetyl, phenylacetyl, α-aminophenylacetyl, phenoxyacetyl, thiophenoxyacetyl, 2-thienylacetyl, tetrazolylacetyl, cyanoacetyl, sydnone-3-acetyl, pyridylthioacetyl, alpha-hydroxyphenylacetyl or alpha-hydroxy-2-thienylacetyl group.

EXAMPLE 10

3-Chloro-3-methyl-8-oxo-7-[2-(2-thienyl)acetamido)]-5-thia-1-azabicyclo[4.2.0]octane-2-carboxylic acid.

The title compound was prepared from the ester of Example 9 by the same procedure as that described in Example 5. The product obtained in 70 per cent yield decomposed above 80°C., nmr (DCCl₃) ppm (δ) 1.73 (s, 3, 3-$CH_3$), 3.20 (ABq, δ 1.0 ppm, J 10 cps, 2-$CH_2$),

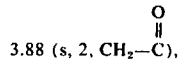
3.88 (s, 2, $CH_2$—C), 4.70 (s, 1, 4—H), 5.26 (d, 1, 6—H), 5.60 (d, 1, 7H), 7.0 (m, 2) and 7.3 (m, 1) (2-thienyl).

Elemental Analysis for $C_{14}H_{15}N_2ClO_4S_2$: Calc'd: C, 44.85; H, 4.03; N, 7.47. Found: C, 44.59; H, 4.19; N, 7.14.

What is claimed is:
1. A compound of the formula:

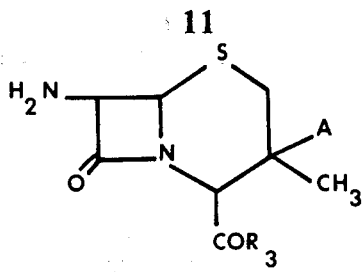

in which
R³ is a member selected from the group consisting of hydroxy, lower alkoxy, 2,2,2-trichloroethoxy, aryloxy of 6 to 10 carbon atoms, aralkoxy of 7 to 12 carbon atoms, alkoxyaralkoxy of 9 to 14 carbon atoms, mono- or di-lower alkylamino, arylamino of 6 to 10 carbon atoms, saccarimido, phthalimido, and OM where M is an alkali metal cation, an alkaline earth metal cation or the ammonium cation;

A is a member selected from the group consisting of —Cl, —Br and —I; and the pharmaceutically acceptable acid addition salts thereof.

2. The compound of claim 1 which is 7-amino-3-chloro-3-methyl-8-oxo-5-thia-1-azabicyclo[4.2.0]octane-2-carboxylic acid, p-nitrobenzyl ester.

* * * * *